United States Patent
Keller et al.

(10) Patent No.: US 8,959,002 B2
(45) Date of Patent: Feb. 17, 2015

(54) CHARACTERIZING AN ELONGATE TEXTILE PRODUCT

(75) Inventors: Beat Keller, Zurich (CH); Stefan Gehrig, Uster (CH); Peter Schmid, Zurich (CH); Loris De Vries, Riedikon (CH)

(73) Assignee: Uster Technologies, AG, Uster (CH)

( * ) Notice: Subject to any disclaimer, the term of this patent is extended or adjusted under 35 U.S.C. 154(b) by 718 days.

(21) Appl. No.: 13/141,411

(22) PCT Filed: Dec. 8, 2009

(86) PCT No.: PCT/CH2009/000390
§ 371 (c)(1),
(2), (4) Date: Jun. 22, 2011

(87) PCT Pub. No.: WO2010/078665
PCT Pub. Date: Jul. 15, 2010

(65) Prior Publication Data
US 2011/0264397 A1 Oct. 27, 2011

(30) Foreign Application Priority Data
Jan. 7, 2009 (CH) .......................................... 16/09

(51) Int. Cl.
*B65H 63/06* (2006.01)
(52) U.S. Cl.
CPC .......... *B65H 63/062* (2013.01); *B65H 2701/31* (2013.01)
USPC ............ 702/127; 700/144; 700/130; 700/131

(58) Field of Classification Search
USPC ........................................................ 702/127
See application file for complete search history.

(56) References Cited

U.S. PATENT DOCUMENTS

| 5,834,639 | A | * | 11/1998 | Meier et al. ...................... 73/159 |
| 6,374,152 | B1 | * | 4/2002 | Wepfer et al. ................. 700/144 |
| 2007/0277495 | A1 | | 12/2007 | Biermann et al. | |
| 2011/0264397 | A1 | * | 10/2011 | Keller et al. .................. 702/127 |

FOREIGN PATENT DOCUMENTS

DE  102007028651 A1  12/2008

* cited by examiner

*Primary Examiner* — Jonathan C Teixeira Moffat
*Assistant Examiner* — Stephanie Chang
(74) *Attorney, Agent, or Firm* — Luedeka Neely Group, P.C.; Rick Barnes

(57) ABSTRACT

Readings of a characteristic of the yarn along the longitudinal direction of the yarn are detected. Values of a yarn parameter are determined from the readings. An event field contains a quadrant of a two-dimensional Cartesian coordinate system, whose abscissa defines an extension of yarn parameter values in the longitudinal direction and whose ordinate defines a deviation of the yarn parameter from a desired value. Densities of events in the event field are determined from the values of the yarn parameter and their extensions in the longitudinal direction. A yarn body is represented as an area in the event field. The area on the one hand is delimited by the abscissa, on the other hand by the ordinate and further by a line in the event field that substantially follows a constant event density. The representation of the yarn body permits a clearing limit to be defined in a rapid and rational manner.

21 Claims, 3 Drawing Sheets

CHARACTERIZING AN ELONGATE TEXTILE PRODUCT

This application claims all rights and priority on prior pending PCT application CH2009/000390 filed Aug. 12, 2009 and prior pending Swiss application 00016/09 filed Jan. 7, 2009. The present invention lies in the field of textile quality control. It relates to a method and to a device for characterizing an elongate, textile product to be tested, according to the preambles of the independent patent claims. Such methods and devices are typically applied to spinning machines and winding machines. The elongate textile product to be tested is preferably yarn, but may also be a sliver or a roving etc.

FIELD

Background

So-called yarn clearers are installed on spinning machines or winding machines for ensuring the yarn quality. Such a device is known e.g. from EP1249422 A2. It contains a measurement head with at least one sensor which scans the moved yarn. Sensor principles which are often applied are the capacitive one (see e.g. EP0924513 A1) or the optical one (see e.g. WO9313407 A1). The aim of the scanning is to detect defect places, such as thick places, thin places or foreign matter in the yarn. The output signal of the sensor is continuously evaluated with predefined assessment criteria. The assessment criteria are usually defined in the form of a clearing limit or clearing curve in a two-dimensional classification field or event field, which is spanned on the one hand by the length of the event and on the other hand by the amplitude of the event, e.g. a deviation of the yarn mass from a desired value. Events below the clearing limit are tolerated, and events above the clearing limit are removed from the yarn or at least registered as defect places.

A method for clearing yarns is known from U.S. Pat. No. 6,374,152 B1, in which the clearing limit is computed automatically on account of the density of the yarn defect and is thus set in an optimal manner. For this purpose, a sufficiently long section of the yarn is measured prior to this. The measured events are represented in the known, two-dimensional classification field as points or crosses. The yarn defect density is computed from the measurement results and is represented in the classification field as a relief. The clearing limit is defined automatically by way of a predefined permissible yarn defect density. It may be continuously readjusted during the control procedure. The measurements are effected in the yarn clearer measurement heads at the individual spinning or winding positions, whilst the computations and closed-loop controls take place in a central computation unit, to which a multitude of yarn clearer measurement heads is connected.

A disadvantage of the method known from U.S. Pat. No. 6,374,152 B1 is to be seen in the fact that the graphic representations of all events and of the yarn defect density relief in the classification field are confusing due to the amount of information. Moreover, large quantities of data are transmitted from the yarn clearer measurement heads to the central computation unit. One thus reaches the technical limits of transmission capacity and data processing.

SUMMARY

It is the object of the present invention to indicate a method and a device for characterizing an elongate textile product to be tested, such as yarn, which provides clear, relevant data on the textile product to be tested. By way of this, an operating person is then put in the position of quickly detecting characteristic characteristics of the textile product to be tested and of rationally setting an optimal clearing limit. A further object is to reduce the data quantity which is to be transmitted from the yarn clearer measurement heads to the central control unit.

Moreover, a method for clearing elongate textile products to be tested such as yarn is to be specified, in which method an optimal clearing limit may be set in a quick and rational manner.

These and other objects are achieved by the method according to the invention and the device according to the invention, according to the independent patent claims. Advantageous embodiments are specified in the dependent patent claims.

The invention is hereinafter explained without any restriction to the generality, by way of an example with yarn. It may just as easily be applied to other elongate textile products to be tested, such a sliver or roving.

According to the invention, a section of the yarn is subjected to measurement. The yarn data coming from the measurement is processed in a suitable manner, in particular summarized, simplified and condensed. A graphic representation of the thus processed yarn data helps the operating person with regard to an intuitive understanding of the yarn clearing in general and of the characteristic characteristics of the examined yarn in particular. It thus permits the operating person to quickly detect characteristic properties of the yarn and to rationally set the clearing limit. This in turn leads to a yarn clearing which is optimized with regard to quality, costs and time.

The invention is based on the knowledge that not all events which are measured in the yarn are equally important for the assessment of the yarn or for defining the clearing limit. The classification field, hereinafter called event field, with regard to this, may be very coarsely divided into three regions as described below.

The first region, in the vicinity of the two axes, i.e. for relatively small event amplitudes and relatively small event lengths, many yarn events occur in a high density which, however, observed individually have a small "intensity" (e.g. event length times the event amplitude) and therefore do not disturb. These events may be considered as statistical "noise." They do not need to be removed from the yarn. Accordingly, they are also not of interest and neither need to be transmitted to the central computation unit nor represented in the event field. This inner region to a certain extent belongs to the "actual yarn" and is therefore indicated as the "yarn body."

The yarn body characterizes the examined yarn in the following context: (a) One may deduce the quality of the yarn and the textile appearance of a textile sheet produced therefrom (woven or knitted fabric) from the size, shape and position of the yarn body in the event field; (b) The yarn quality cannot be improved by way of removing individual events or ones occurring in a cluster, from the yarn body.

The second, middle, band-like region, in which possibly disrupting yarn defects lie, borders the yarn body. The event density in this region is smaller than in the yarn body, but is still significant. Normally, the clearing limit is set in this middle region and separates the allowable form the unallowable yarn defects. Thus the position and density of the events are relevant here.

The third region, with a larger distance from the yarn body, i.e. for relatively large event amplitudes and relatively large defect lengths, the defects intensities are large, but their density is small. For this reason, this outer region is of less significance for the data transmission and the data processing.

Accordingly, in the method according to the invention, for characterizing an elongate textile product to be tested, moved along its longitudinal direction, readings of a characteristic of the textile product to be tested are detected along the longitudinal direction of the textile product to be tested. Values of a parameter of the textile product to be tested are determined from the readings. An event field is set up, which includes a quadrant or a part of a quadrant of a two-dimensional Cartesian coordinate system, whose abscissa indicates the extension of parameter values in the longitudinal direction and whose ordinate indicates a deviation of the parameter from a desired value. Densities of events in the event field are determined from the values of the parameter and their extensions in the longitudinal direction. A body of the product to be tested is represented as an area in the event field. The area on the one hand is delimited by the abscissa or a straight line running parallel thereto, and on the other hand by the ordinate or a straight line running parallel thereto and further by a line in the event field which essentially follows a constant event density.

The area representing the body of the product to be tested is preferably connected. The term "connected" may indeed be understood in the context of mathematical topology. Thereby, in practice, it is of no real significance as to whether the general connectedness or the more particular path connectedness is used for the definition. The area does not need to be simply connected, i.e. it may have recesses enclosed on all sides.

The measured parameters may relate to the mass per length unit, to the diameter, to the reflectivity or the absorptivity of the product to be tested, to foreign matter in the product to be tested or to other characteristics of the product to be tested.

The threshold event density, which corresponds to the line delimiting the body of the product to be tested, should fulfill the following criteria: (a) It is so high that the removal of all events which occur with this or with a lower event density, from the product to be tested would compromise the productivity too greatly, and (b) it is simultaneously so low that it still lies sufficiently close to that defect density which appears to be useful to remove from the product to be tested, e.g. between ten and one hundred times greater.

Threshold event densities suitable in particular for yarn, lie between 500 and 2000 events per 100 km of length of the product to be tested and preferably at 1000 events per 100 km length of the product to be tested.

One or more further areas may connect to the area representing the body of the product to be tested and this further area or areas may likewise be delimited by one or more further lines in the event field, which in each case follows or follow an essentially constant event density. Preferably, the event densities, which are followed by the line delimiting the body of the product to be tested and the further lines, essentially form a geometric sequence.

The area representing the body of the product to be tested and the further areas may graphically differ from their respective surroundings, in particular by way of them having a different color, a different shade of grey or a different pattern than their respective surroundings.

The values of the yarn parameter together with their extensions in the longitudinal direction may be represented as events in the event field. Thereby, preferably no events are represented in the body of the product to be tested or at least part of the body of the product to be tested, said part being adjacent the abscissa or the straight line running parallel thereto. For this, the event field may be divided by a classification limit into two classification regions, wherein no events are represented in a first classification region, and events are represented in a second classification region. The classification limit preferably follows an essentially constant event density.

In the method according to the invention, for clearing defects from an elongate textile product to be tested which is moved along its longitudinal direction, readings of a characteristic of the textile product to be tested are detected along the longitudinal direction of the textile product to be tested, for characterizing the textile product to be tested. Values of a parameter of the textile product to be tested are determined from the readings. An event filed is provided, which contains a quadrant or a part of a quadrant of a two-dimensional Cartesian coordinate system, whose abscissa represents an extension of parameter values in the longitudinal direction and whose ordinate represents a deviation of the parameter from a desired value. Densities of events in the event field are determined from the values of the parameter and their extensions in the longitudinal direction. A body of the product to be tested is represented as an area in the event field, and this area on the one hand is delimited by the abscissa or a straight line running parallel thereto, and on the other hand by the ordinate or a straight line running parallel thereto and further by a line in the event field, which essentially follows a constant event density. The event field is divided by way of at least one clearing limit or clearing curve into clearing regions, of which a first clearing region defines allowable events and a second clearing region defines unallowable events. The previously carried out characterization of the textile product to be tested influences the fixing of the clearing limit.

The first clearing region and the second clearing region may differ graphically from one another, in particular by way of them having different colors, different shades of grey or different patterns. The number of unallowable events and the number of unallowable events per length unit of the textile product to be tested may be computed by way of the readings of yarn parameter on the one hand and the clearing limit on the other hand, and outputted. These are important details for the operating person, since the number of cuts per length of product to be tested influences on the one hand the quality of the product to be tested and on the other hand the productivity. The number of cuts per length of product to be tested may be reduced or increased by way of changing the clearing limit. By way of a trial changing of the clearing limit, the operating person may find that clearing limit which optimally corresponds to the requirements of the operation with regard to quality costs and time. Thereby, no product to be tested is wasted for trials, since the trials take place in a virtual manner by way of computation on the basis of the measured parameter values and starting from the represented body of the product to be tested.

In the first clearing region, at least one first exclusion region may be defined, which defines unallowable events. Such first exclusion regions may e.g. be defined for clusters of events which individually would per se be allowable, but in a clustered manner would disturb and therefore are undesirable. Likewise, at least one second exclusion region which defines allowable events may be defined in the second clearing region. Such second exclusion regions may e.g. be defined for effects, which on clearing effect yarn, must not erroneously be considered as yarn defects and must not be cleared out.

The event field does not need to be limited to a single quadrant. It may additionally contain at least one further quadrant or a part of a further quadrant.

Certain support values of the respective density curve may be stored for the numerical handling of the density curves which are used for the delimitations of the area representing the body of the product to be tested and the further areas. In each case, one may carry out a suitable interpolation, or an extrapolation at the edge, between the stored support values.

The body of the product to be tested, the further areas, the classification regions and the clearing regions may be automatically adapted to the continuous detection of the readings and to the changes of densities of the events in the event field which result therefrom.

The device according to the invention, for characterizing an elongate textile product to be tested which is moved along it longitudinal direction, contains a measurement head for detecting readings of a characteristic of the textile product to be tested as well as for determining values of a parameter of the textile product to be tested from the readings. It further contains a control unit which is connected to the measurement head. The control unit comprises a memory unit and an output unit for storing and outputting, respectively, an event field which contains a quadrant or a part of a quadrant of a two-dimensional Cartesian coordinate system whose abscissa represents an extension of parameter values in the longitudinal direction and whose ordinate a deviation of the parameter from a desired value, and a computation unit for determining densities of events in the event field from the values of the parameter and their extensions in the longitudinal direction. The control unit is set up for outputting a body of the product to be tested as an area in the event field. The area on the one hand is delimited by the abscissa or a straight line running parallel thereto, on the other hand by the ordinate or a straight line running parallel thereto and further by way of a line in the event field which essentially follows a constant event density.

The device according to the invention is applied in a textile processing machine, for example in a spinning machine or a winding machine for yarn. Such a textile processing machine typically comprises a multitude of working positions. Accordingly, the device according to the invention may contain a multitude of measurement heads which are located at each working position. The measurement heads are all connected to the central control unit, e.g. via a serial bus such as e.g. RS-485. An interface transducer may be installed between a respective measurement head and the control unit. The control unit is preferably installed in the textile processing machine. This has the advantage that the person who operates the textile processing machine, may carry out the setting of the clearing limit at his or her workplace, and that no additional computer is required. The device according to the invention may contain a cutting device for removing unallowable events from the yarn, at every working position, in the vicinity of every measurement head.

DRAWINGS

The invention is hereinafter explained in a detailed manner by way of the example of a winding machine for yarn, and by way of the drawings.

FIG. 1 schematically depicts a winding machine with a yarn clearer system.

DETAILED DESCRIPTION

Figure 1:
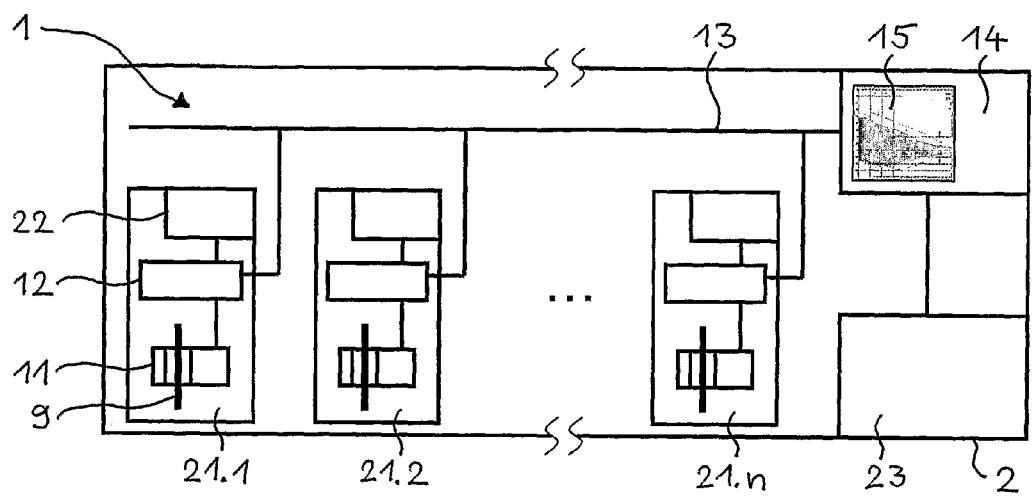

A winding machine 2 with several winding positions 21.1, 21.2, . . . , 21.$n$ is represented very schematically in FIG. 1. A device 1 according to the invention is installed into the winding machine 2. Yarn 9 is monitored by a measurement head 11 of the device 1 according to the invention, during the winding procedure, at each winding position 21.1. The measurement head 11 contains a sensor, with which a characteristic of the yarn 9 is measured, e.g. a capacitive sensor for measuring a dielectric characteristic of the yarn 9. Moreover, the measurement head 11 contains an evaluation unit which is set up to determine a yarn parameter, e.g. the yarn mass per length unit, from the readings. The measurement head 11 is connected via an interface transducer 12 to a central control unit 14 of the device 1 according to the invention. The measurement head 11 is set and controlled by the control unit 14 via the connection, and the measurement head 11 transmits data such as the determined yarn parameters to the control unit 14. A connection lead 13 between all interface transducers 12 and the control unit 14 may be designed as a serial bus such as e.g. RS-485. The interface transducer 12 may additionally also be connected to a winding-position computer 22 of the respective winding position 21.1. The control unit 14 comprises an output unit and an input unit for the operating person. Preferably, the output unit and the input unit are designed together as a touchscreen 15. The control unit 14 is connected to a control computer 23 of the winding machine 2. Instead of in the control unit 14, the output unit or the input unit may be installed in the winding machine 2, e.g. in the control computer 23.

Figure 2:
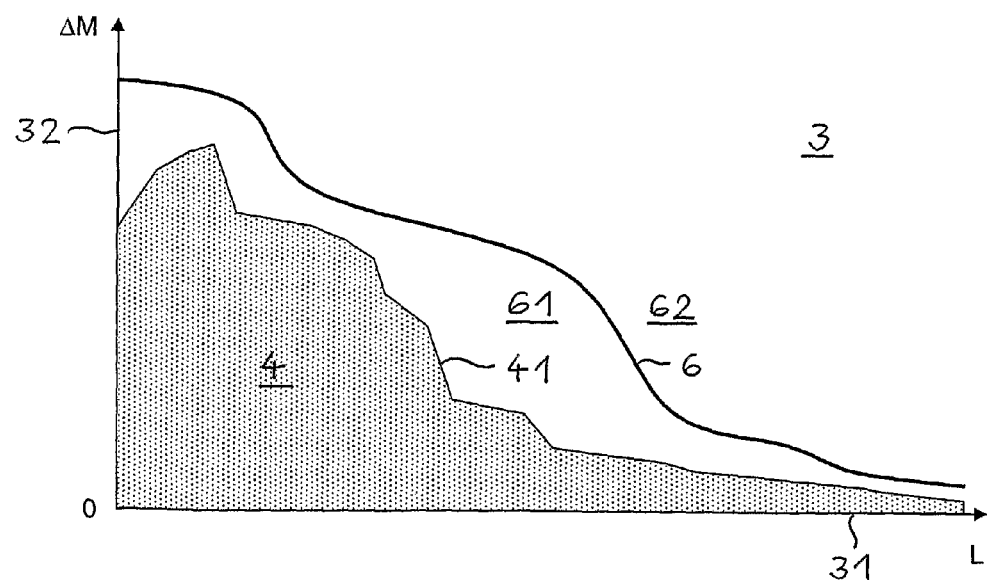
FIG. 2 depicts an event field with a yarn body and a clearing curve, as may result from a method according to the invention.

FIG. 2 shows a possible event field 3 with a yarn body and a clearing limit 6, as may be represented on the output unit 15 of the control unit 14. The event field 3 is a quadrant of a two-dimensional Cartesian coordinate system which is spanned by an abscissa 31 and an ordinate 32. The ordinate 32 specifies a deviation $\Delta M$ of the yarn parameter, e.g. the deviation of the yarn mass per length unit, from a desired value. The desired value is preferably determined by a continuous average formation over a multitude of measurements. The abscissa 31 indicates over which length L along the yarn longitudinal direction a deviation $\Delta M$ extends. A determined deviation $\Delta M$ and its length L together form the coordinates of a yarn event which defines a point in the event field 3 and may be represented there in a suitable manner (cf. FIG. 3).

An adequately long yarn section is measured in a calibration procedure. A calibration length of at least approx. one kilometer is seen as "sufficient;" larger calibration lengths of e.g. 10 km or 100 km are however preferred, since they provide results which statistically provide better information. The values of the yarn parameter $\Delta M$ and the associated lengths L are transferred from the measurement head 11 to the control unit 14. Densities of events in the event field 3 are determined from this in a computation unit of the control unit 14, as is described e.g. in U.S. Pat. No. 6,374,152 B1. In this manner, an event density may be assigned to each point of the event field 3 in an unambiguous manner. Local changes of the thus determined event density function which are possibly caused by measurement errors or other artifacts and which are too abrupt, may be avoided by way of interpolation, extrapolation, smoothing and other numerical methods.

According to the invention, a yarn body is computed from the event density function and is represented as an area 4 in the event field 3. A sufficiently high threshold event density of e.g. 1000 events per 100 km yarn length is selected. The connection of all points in the event field 3, to which the threshold event density is assigned, results in a density curve 41 which delimits the yarn body from the remaining event field 3. The yarn body is delimited towards the two coordinate axes 31, 32, by the coordinate axes 31, 32 themselves. A connected area 4, which is characteristic of the measured yarn 9, arises by way of these delimitations. The area 4 representing the yarn body differs graphically from the remaining event field 3 by way of it e.g. having a different color, a different shade of grey or a different pattern than the remaining event field 3.

The computation and representation of the yarn body, according to the invention, permit the operating person to rapidly and intuitively perceive the characteristics of the examined yarn 9. This permits the operating person to rapidly and rationally set a clearing curve 6 for clearing defects out of the yarn 9. The clearing curve 6 is that line which divides the event field 3 into clearing regions 61, 62, of which a first clearing region 61 defines allowable events and a second clearing region 62 unallowable events. It is the graphic representation of a clearing limit, i.e. of a criterion for the assessment of the yarn quality. The setting of the clearing limit or of the clearing curve 6 is affected preferably via the input unit 15 at the control unit 14. Thereby, the control unit 14 may suggest a standard clearing curve, e.g. as a further density curve with a significantly lower event density than the threshold event density 41 for the yarn body 4. The clearing curve 6 should lie above the yarn body 4, since it would not make sense to want to clear events out of the yarn body 4. The operating person may change the standard clearing curve by way of inputs at the input unit 15. Alternatively, the operating person by way of inputs at the input unit 15 may define the clearing curve 6 according to his or her own experiences, without starting from a suggestion of the control unit 14.

Figure 3:
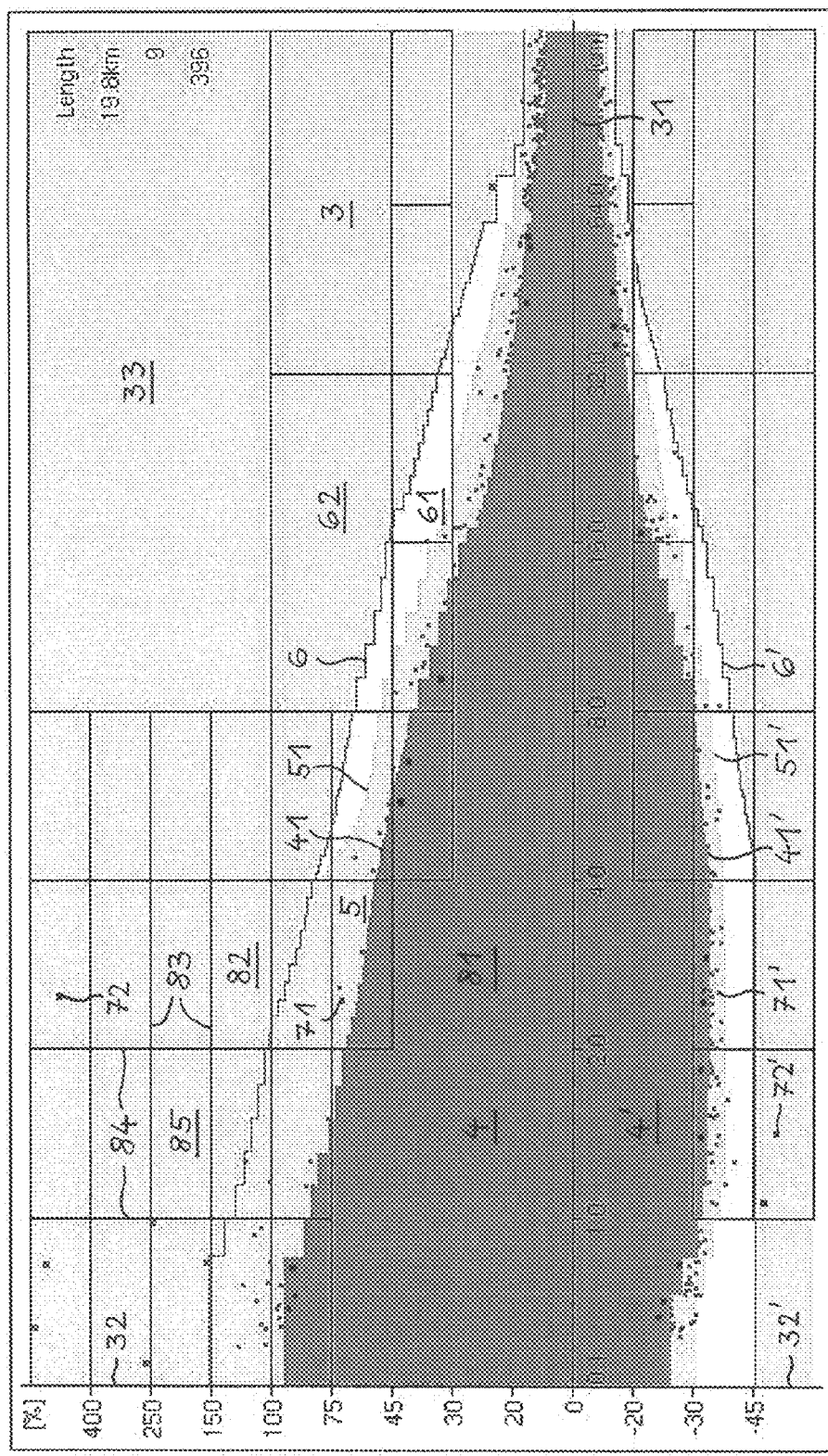
FIG. 3 depicts an event field with yarn events, a yarn body and a clearing limit, as may result from a method according to the invention.

FIG. 3 shows an extended illustration of an event field 3, as may be outputted on the output unit 15 of the control unit 14. Here, the event field 3 not only contains the first, but additionally also yet the fourth quadrant. In the first quadrant, thick places which are caused by the local increase of the mass, and in the fourth quadrant, thin places caused by the local reduction of mass, are plotted versus the respective length L. Due to the fact that the length axes 31 of the two quadrants coincide, the yarn body 4 for the thick places and the yarn body 4' for the thin places visually join up into a single complete yarn body. This is not necessarily symmetrical with respect to the abscissa 31. The axes 31, 32, 32' for the length and mass increase or mass reduction are preferably scaled in a logarithmic, almost logarithmic or partly logarithmic manner.

In the example of FIG. 3, a further area 5 connects to the area 4 representing the yarn body. The further area 5 is delimited by the density curve 41 delimiting the yarn body and by a further density curve 51 which corresponds to a lower event density. The higher event density may e.g. be 1000 events per 100 km of yarn length and the lower event density e.g. 100 events per 100 km of yarn length. The two event densities are thus part of the geometric sequence 1, 10, 100, 1000, . . . events per 100 km of yarn length. The area 4 representing the yarn body and the further area 5 differ graphically from one another and from their respective surroundings. Thus e.g. the area 4 representing the yarn body may be colored dark-green and the further area 5 may be colored light-green. Instead of only one further area 5, one may also represent several further areas. Such further areas 5 may help the operating person to perceive the character of the yarn 9 even better and to optimally set the clearing limit 6.

A clearing curve 6 is also drawn in the event field 3 of FIG. 3. It separates a first clearing region 61 which defines allowable events, and a second clearing region 62 which defines unallowable events. The two clearing regions 61, 62 are preferably colored differently, e.g. the first clearing region 61 is colored white and the second clearing region 62 is colored grey. The clearing curve 6 is basically independent of the density curves 41, 51, although it would keep to them with regard to its coarse course. In FIG. 3, the clearing curve 6 partly coincides with the further density curve 51, and partly does not.

Moreover, events 71, 72 in the form of squares are drawn in the event field 3 of FIG. 3. Thereby, the symbols for the allowable events 71 in the first clearing region 61 nearside of the clearing curve 6 may differ from those for the unallowable events 72 in the second clearing region 62 far side of the clearing curve 6, e.g. by way of their size or their color. The events together form a so-called scatter plot.

Not all measured events are registered in the event field 3. The largest part of the yarn body is free of events. The reason for this is that events in the yarn body are just not of any interest to the operating person. They "belong to the yarn." The non-representation of those events which lie in the proximity of the abscissa 31 at least has the following two advantages: (a) These events do not need to be transmitted from the measurement head 11 to the control unit 14. Thus the data quantity which is to be transmitted and processed is significantly reduced and the data leads as well as the control unit 14 are relieved. The capacities which become free on account of this may be used for more important things. (b) The graphic representation contains less event points and becomes clearer due to this. The operating person is not distracted by unnecessary event points and may concentrate on that which is important.

The event field 3 is thus divided into two classification regions 81, 82: into a first classification region 81, in which no events are represented, and into a second classification region 82, in which the events are represented. The two classification regions 81, 82 are delimited from one another by way of a classification limit. The classification limit is not drawn in the example of FIG. 3. Its course may be suspected only by way of the events 71 which are still represented. It also preferably follows a density curve which may correspond to a higher, equal or lower event density than the density curve 41 delimiting the yarn body 4.

The second classification region 82 is divided by way of horizontal classification limits 83 and vertical classification limits 84 into rectangular classes 85 for yarn events 71, 72. Such classes 85 to the first extent serve for an improved statistical perception of similar events 71, 72. Thus e.g. the ascertained events 71, 72 in each class 85 are counted and the results are outputted in classes. More usefully, the classes 85 are only represented in the second classification region 82, in which events are represented at all. However, it would also be possible to subdivide the entire event field 3 into such classes 85

That which has been described for the first quadrant of the event field 3 of FIG. 3, analogously also applies to the fourth quadrant. The corresponding elements in the fourth quadrant are indicated with the same reference numerals as in the first quadrant and an additional apostrophe.

In FIG. 3, one finds the following exemplary details in a description field 33: (a) The yarn length, on account of which the density curves 41, 42 for the yarn body 4 and the further area 5 have been determined, was 19.8 km. (b) The number of events 72 which lie in the two second clearing regions 62 and thus would be removed as defects from the yarn section of 19.8 km length is 9. Thus 45 cuts per 100 km yarn length would result, said cut number likewise being able to be displayed if required. (c) The total number of events 71, 72 registered in the event field 3 is 396.

Figure 4:
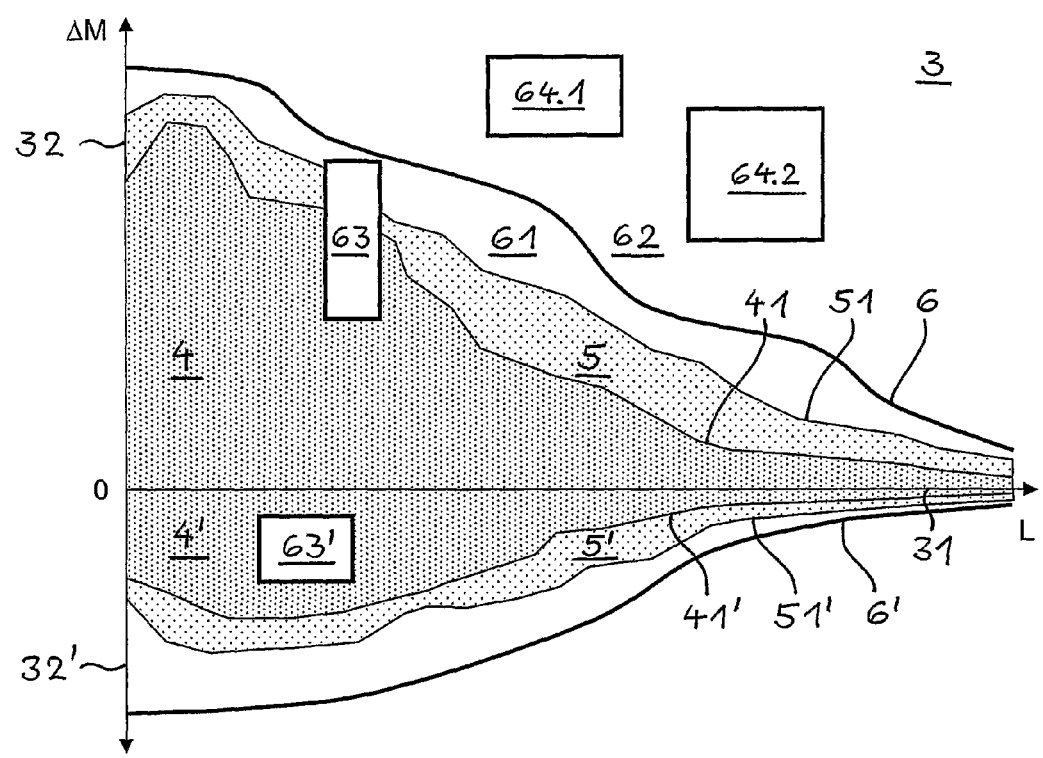
FIG. 4 depicts a further event field with a yarn body and with a clearing curve, as may result from a method according to the invention.

A further representation of an event field 3 is shown in FIG. 4. Many elements are already known from the FIGS. 2 and 3, are indicated in FIG. 4 with the same reference numerals and here do not need to be explained again, thus the fourth quadrant for thin places, the yarn body 4, the further area 5 and the clearing curve 6. In contrast to the previous FIGS. 2 and 3, exclusion regions 63, 63', 64.1, 64.2 are defined in the event field 3 of FIG. 4. In such an exclusion region 63, 63', 64.1, 64.2, the allowability criterion for yarn events 71, 72 is inverted with respect to its surroundings, as described below.

Events which lie in a first exclusion region 63, 63' lying in the first clearing region 61 are unallowable. Such first exclusion regions 63, 63' may be defined e.g. for clusters of events 71, which individually would per se be allowable, but in a clustered manner would disturb and are therefore undesirable. The first exclusion regions 63, 63' could be located completely or partly in the yarn body 4 or outside the yarn body 4, in any case however in the first clearing region 61. The yarn body 4' which is located in the fourth quadrant, with its first exclusion region 63' which is enclosed on all sides, forms an example of a 2-connected area in the context of mathematical topology. In contrast, the previously discussed yarn bodies 4 are simply connected and also path connected.

Events which lie in a second exclusion region 64.1, 64.2 lying in the second clearing region 62, are allowable. Such second exclusion regions 64.1, 64.2 may e.g. be defined for effects which, with the clearing of defect yarn, must not erroneously be considered as yarn defects and must not be cleared out.

Of course the present invention is not limited to the embodiments discussed above. With the knowledge of the invention, the man skilled in the art would be able to derive further variants which also belong to the subject matter of the present invention.

LIST OF REFERENCE NUMERALS 1 device
11 measurement head
12 interface transducer
13 connection lead
14 control unit
15 touchscreen as input and output unit
2 winding machine
21.1, 21.2, . . . winding positions
22 winding-position computer
23 control computer
3 event field
31 abscissa
32 ordinate
4 yarn body, the area representing the yarn body
41 density curve delimiting the event field
5 further area
51 density curve delimiting the further area
6 clearing limit or clearing curve
61 first clearing region
62 second clearing region
63 first exclusion region
64.1, 64.2 second exclusion region
71 allowable event
72 unallowable event
81 first classification region
82 second classification region
83 horizontal class limit
84 vertical class limit
85 class
9 yarn

The invention claimed is:

1. A processor-based method for characterizing an elongate textile product to be tested that is moved along its longitudinal direction, the method comprising the steps of:
   detecting readings of a characteristic of the elongate textile product to be tested along the longitudinal direction of the elongate textile product to be tested with a sensor,
   determining, with a processor, values of a parameter of the elongate textile product to be tested from the readings,
   providing an event field that contains at least a part of a quadrant of a two-dimensional Cartesian coordinate system, having an abscissa that defines an extension of parameter values in the longitudinal direction and an ordinate that defines a deviation of the parameter from a desired value, and
   determining densities of events in the event field from the values of the parameter and their extensions in the longitudinal direction,
   wherein a body of the elongate textile product to be tested is represented in the event field as an area that is delimited by one of the abscissa and a first straight line running parallel thereto, by one of the ordinate and a second straight line running parallel thereto, and by a third line in the event field that follows a constant event density.

2. The method according to claim 1, wherein the constant event density lies between 500 and 2000 events per 100 kilometer length of the elongate textile product to be tested.

3. The method according to claim 1, wherein at least one further area connects to the area representing the body of the elongate textile product to be tested, and is delimited by at least one further line in the event field that follows a constant event density.

4. The method according to claim 3, wherein the event densities that are followed by the third line delimiting the body of the elongate textile product to be tested and the further line form a geometric sequence.

5. The method according to claim 3, wherein at least one of the area representing the body of the elongate textile product to be tested and the further area differ graphically from their respective surroundings by at least one of a different color, a different shade of gray, and a different pattern than their respective surroundings.

6. The method according to claim 1, wherein the values of the parameter and their extensions in the longitudinal direction are represented as events in the event field.

7. The method according to claim 6, wherein no events are represented in a part of the body of the elongate textile product to be tested that is adjacent at least one of the abscissa and the first straight line running parallel thereto.

8. The method according to claim 7, wherein the event field is divided by a classification limit into two classification regions, and no events are represented in a first of the two classification regions, and events are represented in a second of the two classification regions.

9. The method according to claim 8, wherein the classification limit follows a constant event density.

10. A processor-based method for clearing defects from an elongate textile product to be tested that is moved along its longitudinal direction, the method comprising the steps of:

detecting readings of a characteristic of the elongate textile product to be tested along the longitudinal direction of the elongate textile product to be tested with a sensor, determining, with the processor, values of a parameter of the elongate textile product to be tested from the readings, providing an event field that contains at least a part of a quadrant of a two-dimensional Cartesian coordinate system, having an abscissa that defines an extension of parameter values in the longitudinal direction and an ordinate that defines a deviation of the parameter from a desired value, and which is divided by at least one clearing curve into clearing regions, of which a first clearing region defines allowable events and a second clearing region defines unallowable events, and determining densities of events in the event field from the values of the parameter and their extensions in the longitudinal direction, wherein a body of the elongate textile product to be tested is characterized in the event field as an area that is delimited by one of the abscissa and a first straight line running parallel thereto, by one of the ordinate and a second straight line running parallel thereto, and by a third line in the event field that follows a constant event density, and the setting of the clearing curve is determined at least in part by the characterization.

11. The method according to claim 10, wherein the first clearing region and the second clearing region graphically differ for one another by at least one of a different color, a different shade of gray, and a different pattern than their respective surroundings.

12. The method according to claim 10, wherein at least one of the number of unallowable events and the number of unallowable events per length unit of the elongate textile product to be tested are computed based at least in part on a yarn parameter and the clearing curve, and outputted.

13. The method according to one of the claim 10, wherein at least one first exclusion region is defined in the first clearing region and defines unallowable events, and at least one second exclusion region is defined in the second clearing region and defines allowable events.

14. The method according to claim 10, wherein the event field contains at least a part of an additional quadrant.

15. The method according to claim 10, wherein the event field is divided by a classification limit into two classification regions, and no events are represented in a first of the two classification regions, and events are represented in a second of the two classification regions, and at least one of the body of the elongate textile product to be tested, the further areas, the classification regions, and the clearing regions are automatically adapted to the continuous detection of the readings and to the changes of densities of events in the event field, the changes resulting therefrom.

16. A device for characterizing an elongate textile product to be tested moved along its longitudinal direction, comprising:

a measurement head for detecting readings of a characteristic of the elongate textile product to be tested along the longitudinal direction of the elongate textile product to be tested as well as for determining values of a parameter of the elongate textile product to be tested from the readings, and a control unit connected to the measurement head, the control unit comprising:

a memory unit and an output unit for storing and outputting, respectively, an event field that contains at least a part of a quadrant of a two-dimensional Cartesian coordinate system, having an abscissa that defines an extension of parameter values in the longitudinal direction and an ordinate that defines a deviation of the parameter from a desired value, and a computation unit for determining densities of events in the event field from the values of the parameter and their extensions in the longitudinal direction, wherein the control unit is set up for outputting the body of the elongate textile product to be tested as an area in the event field that is delimited by at least one of the abscissa and a first straight line running parallel thereto, by at least one of the ordinate and a second straight line running parallel thereto, and by a third line in the event field that follows a constant event density.

17. The device according to claim 16, wherein the output unit is designed as a screen.

18. The device according to claim 16, wherein the control unit contains an input unit for inputting at least one clearing limit.

19. The device according to claim 18, wherein the output unit and the input unit are designed as a touchscreen.

20. The device according to claim 16, wherein the control unit is installed in a textile processing machine.

21. The device according to claim 16, further comprising a cutting device for removing unallowable events from the elongate textile product to be tested.

* * * * *